US010946037B1

(12) United States Patent
Im et al.

(10) Patent No.: US 10,946,037 B1
(45) Date of Patent: Mar. 16, 2021

(54) PHARMACEUTICAL COMPOSITION FOR THE PREVENTION OR TREATMENT OF NICOTINE ADDICTION AND WITHDRAWAL SYMPTOMS INCLUDING MIRNA

(71) Applicant: KOREA INSTITUTE OF SCIENCE AND TECHNOLOGY, Seoul (KR)

(72) Inventors: Heh-In Im, Seoul (KR); Byung Sun Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 16/927,193

(22) Filed: Jul. 13, 2020

Related U.S. Application Data

(62) Division of application No. 16/842,310, filed on Apr. 7, 2020, now Pat. No. 10,751,360.

(30) Foreign Application Priority Data

Oct. 23, 2019 (KR) .......................... 10-2019-0131816

(51) Int. Cl.
| | |
|---|---|
| *A61K 48/00* | (2006.01) |
| *C07H 21/04* | (2006.01) |
| *A61K 31/7105* | (2006.01) |
| *A61P 25/34* | (2006.01) |
| *C12N 15/113* | (2010.01) |
| *C12N 15/86* | (2006.01) |
| *A61K 9/00* | (2006.01) |

(52) U.S. Cl.
CPC .......... *A61K 31/7105* (2013.01); *A61P 25/34* (2018.01); *C12N 15/113* (2013.01); *C12N 15/86* (2013.01); *A61K 9/0019* (2013.01)

(58) Field of Classification Search
CPC .......... C12N 2310/141; C12N 2320/10; C12N 15/113
See application file for complete search history.

(56) References Cited

U.S. PATENT DOCUMENTS

| | | | |
|---|---|---|---|
| 5,580,859 | A | 12/1996 | Felgner et al. |
| 5,589,466 | A | 12/1996 | Felgner et al. |
| 5,679,647 | A | 10/1997 | Carson et al. |
| 5,736,524 | A | 4/1998 | Content et al. |
| 5,739,118 | A | 4/1998 | Carrano et al. |
| 5,804,566 | A | 9/1998 | Carson et al. |

FOREIGN PATENT DOCUMENTS

| | | |
|---|---|---|
| KR | 10-0656836 B1 | 12/2006 |
| WO | 98/04720 A1 | 2/1998 |

OTHER PUBLICATIONS

BaekSun Kim et al., "Striatal cholinergic interneurons control nicotine reward and somatic withdrawal" The 10th IBRO World Congress of Neuroscience, Daegu, Korea, Sep. 21-25, 2019.
Jon A. Wolff et al., "Direct Gene Transfer into Mouse Muscle in Vivo", Science, vol. 247, pp. 1465-1468, Mar. 23, 1990.
Kirk R. Thomas and Mario R. Capecchi, "Site-Directed Mutagenesis by Gene Targeting in Mouse Embryo-Derived Stem Cells", Cell, vol. 51, pp. 503-512, Nov. 6, 1987.

*Primary Examiner* — Amy H Bowman
(74) *Attorney, Agent, or Firm* — Rabin & Berdo, P.C.

(57) ABSTRACT

Disclosed is a pharmaceutical composition for preventing or treating nicotine addiction or withdrawal symptoms. The pharmaceutical composition includes miR-137 as an active ingredient. Overexpression of miR-137 in an animal model having nicotine addiction or withdrawal symptoms results in relief, prevention or amelioration of the symptoms. Therefore, the use of miR-137 contributes to the prevention or treatment of nicotine addiction or withdrawal symptoms and is expected to be useful for developing relevant therapeutic agents.

2 Claims, 3 Drawing Sheets
Specification includes a Sequence Listing.

PHARMACEUTICAL COMPOSITION FOR THE PREVENTION OR TREATMENT OF NICOTINE ADDICTION AND WITHDRAWAL SYMPTOMS INCLUDING MIRNA

CROSS-REFERENCE TO RELATED APPLICATIONS

This application is a division of U.S. application Ser. No. 16/842,310, filed on Apr. 7, 2020 (allowed on Jun. 9, 2020), which priority under 35 U.S.C. § 119 to Korean Patent Application No. 10-2019-0131816 filed on Oct. 23, 2019 in the Korean Intellectual Property Office, the disclosure of which is incorporated herein by reference in its entirety.

SEQUENCE LISTING SPECIFIC REFERENCE

This application contains a Sequence Listing submitted via EFS-Web and hereby incorporated by reference in its entirety. The Sequence Listing is named 08_CHIP-167-KIST_SEQCRF.txt, created on Apr. 7, 2020, and 646 bytes in size.

BACKGROUND OF THE INVENTION

Field of the Invention

The present invention relates to a pharmaceutical composition for preventing or treating nicotine addiction or withdrawal symptoms including a miRNA as an active ingredient, and more specifically to a pharmaceutical composition for preventing or treating nicotine addiction or withdrawal symptoms including miR-137 as a pharmaceutically active ingredient and at least one pharmaceutically acceptable carrier.

Description of the Related Art

Nicotine is a precursor of nitrosamines, including 4-(methylnitrosamino)-1-(3-pyridyl)-1-butanone (NKK), and is a potent environmental toxin. Symptoms of acute nicotine toxicity include miosis, blurry vision, vomiting, dyspnea, excessive salivation, excessive secretions from the respiratory tract, and reduced heart rate. For chronic addiction, nicotine is accumulated in the body to cause many circulatory diseases. Nicotine in tobacco is a major addictive substance and causes smokers to want more cigarettes due to its powerful addictive properties as they smoke more frequently. Nicotine is generally excreted from the body 2-3 days after absorbed into the body but smokers who have smoked for a longer time have greater difficulty in quitting smoking because of the higher content of nicotine accumulated in the body.

Nicotine enters the brain rapidly through the bloodstream and stimulates nicotinic acetylcholine receptors in the brain to cause the release of dopamine, which in turn activates the reward center in the brain. When trying to stop smoking, the reward response is lost and withdrawal symptoms, including cognitive impairments, occur. Such withdrawal symptoms are relieved by the absorption of nicotine when smoking.

Many therapies have been developed for nicotine addiction. First therapies for nicotine addiction are non-vaccine therapies such as nicotine transdermal patches and nicotine chewing gums. These therapies are called "nicotine replacement therapies (NRT)" and play a role in replacing the amount of nicotine received from smoking and weaning users from nicotine. However, several drawbacks are found in the therapies. Particularly, the penetration of nicotine into the bloodstream through nicotine transdermal patches or chewing gums is reduced, resulting in an increase in the desire to smoke. Problems such as mouth ulcer, pain in the chin, and nausea are encountered in the use of nicotine gums. The use of nicotine transdermal patches is responsible for problems such as dermatitis, sleep disorder, and hypersensitivity. Second therapies for nicotine addiction are based on the use of antibody produced in response to nicotine. These therapies focus on vaccines that stimulate immune systems to produce anti-nicotine antibodies. Anti-nicotine antibodies bind to nicotine in the bloodstream to reduce the amount and proportion of nicotine entering the brain. The therapies do not cause rejection reactions in most subjects and are very effective in treating nicotine addiction. However, antibodies necessary for the treatment of nicotine addiction differs significantly in price from person to person and are clearly limited in their use for prophylactic or therapeutic purposes due to their short duration.

PRIOR ART DOCUMENTS

Patent Documents

Patent Document 1: Korean Patent No. 10-0656836

SUMMARY OF THE INVENTION

The present invention has been made in an effort to solve the above problems, and it is one object of the present invention to provide a pharmaceutical composition for preventing or treating nicotine addiction or withdrawal symptoms.

It is a further object of the present invention to provide a method for treating nicotine addiction or withdrawal symptoms including administering miR-137 or an expression vector containing miR-137 to a patient or smoker suffering from nicotine addiction or withdrawal symptoms.

It is another object of the present invention to provide a method for screening a candidate for preventing or treating nicotine addiction or withdrawal symptoms.

The present invention provides a pharmaceutical composition for preventing or treating nicotine addiction or withdrawal symptoms including, as an active ingredient, miR-137 or an expression vector containing miR-137.

The present invention also provides a method for treating nicotine addiction or withdrawal symptoms including administering miR-137 or an expression vector containing miR-137 to a patient or smoker suffering from nicotine addiction or withdrawal symptoms.

The miR-137 may be an mRNA having the sequence set forth in SEQ ID NO: 1.

The present invention also provides a method for screening a candidate for treating nicotine addiction or withdrawal symptoms including a) treating an animal model having nicotine addiction or withdrawal symptoms with a candidate, b) measuring the expression level of miR-137 in the animal model treated with the candidate, and c) determining whether the candidate increases the expression level of miR-137 compared to an untreated control.

According to the present invention, overexpression of miR-137 in an animal model having nicotine addiction or withdrawal symptoms leads to a reduction in nicotine addiction and withdrawal symptoms caused by nicotine addiction. Therefore, the use of miR-137 contributes to the prevention or treatment of nicotine addiction or withdrawal symptoms and is expected to be useful for screening a relevant candidate.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE INVENTION

Figure 1:
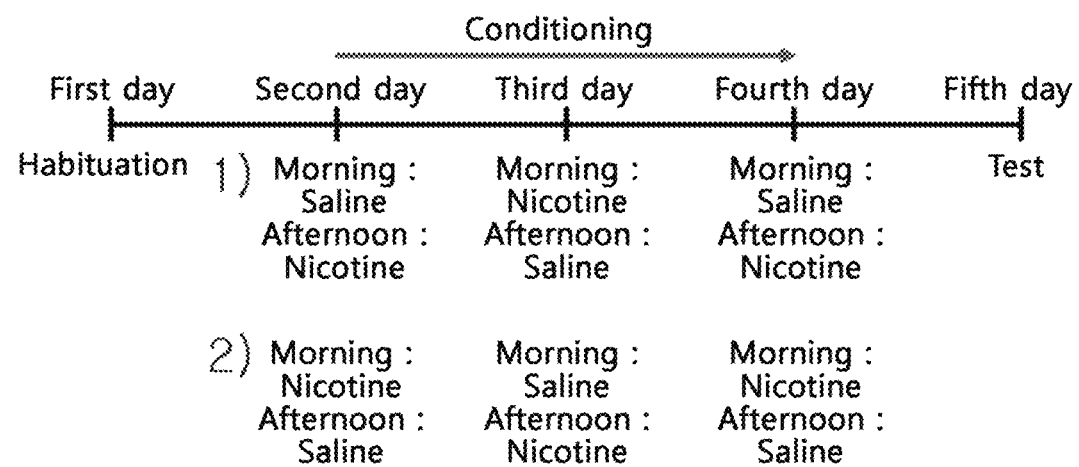
FIG. 1 schematically shows an experimental design for a conditioned place preference.

Several aspects and various embodiments of the present invention will now be described in more detail.

One aspect of the present invention is directed to a pharmaceutical composition for preventing or treating nicotine addiction or withdrawal symptoms including, as an active ingredient, miR-137 or an expression vector containing miR-137.

A further aspect of the present invention is directed to a method for treating nicotine addiction or withdrawal symptoms including administering miR-137 or an expression vector containing miR-137 to a patient or smoker suffering from nicotine addiction or withdrawal symptoms.

The present inventors have succeeded in screening a miRNA associated with nicotine addiction and withdrawal symptoms caused by nicotine addiction and found that overexpression of miR-137 under the above conditions using a recombinant vector reduces nicotine preference and ameliorates withdrawal symptoms. The present invention has been accomplished based on this finding.

Therefore, the present invention provides a pharmaceutical composition for preventing or treating nicotine addiction or withdrawal symptoms including miR-137 as an active ingredient and a method for treating nicotine addiction or withdrawal symptoms including administering a composition including miR-137 as an active ingredient to a subject in need of treatment.

The miR-137 is a polynucleotide having the sequence set forth in SEQ ID NO: 1 or a miRNA including the polynucleotide but is not particularly limited thereto.

As used herein, the terms "preventing", "ameliorating", and "treating" mean to reverse or alleviate not only nicotine addiction symptoms but also nicotine withdrawal symptoms caused after quitting nicotine or to inhibit, delay or prevent the progress of the symptoms. The term "treating" refers to an action of treatment in the meaning of "therapy".

As used herein, the term "nicotine addiction" refers collectively to poisoning caused when highly addictive nicotine is administered or taken and is intended to include acute and chronic addiction. Chronic nicotine addiction is defined as a state in which a person has lost the power of self-control to continuously seek or take nicotine despite an emotional state such as physical or mental impairment. That is, chronic nicotine addiction refers to long-term exposure to nicotine.

The term "withdrawal" refers collectively to symptoms of various mental disorders caused as a result of craving for nicotine during the withdrawal period without taking nicotine in a state in which highly addictive nicotine is repeatedly administered and nicotine dependence is high.

In the Examples section that follows, the miR-137 was demonstrated to exhibit efficacy in preventing or treating nicotine addiction or withdrawal symptoms due to its ability to regulate a gene playing a major role in nicotine addiction or withdrawal symptoms.

The miR-137 may be a mature miRNA. Alternatively, the miR-137 may be a miRNA precursor in the form of a precursor miRNA, pri-miRNA or plasmid.

The miRNA precursor may partially include a phosphorothiolate structure obtained by substituting the RNA phosphate backbone structure with one or more other elements such as sulfur. The RNA may be wholly or partially substituted with DNA, peptide nucleic acid (PNA), and locked nucleic acid (LNA) molecule. The 2'-hydroxyl groups of the RNA substrate may be substituted with various functional structures. Such modification includes, but not limited to, methylation, methoxylation, and fluorination.

The miRNA may be single or double stranded. The mature miRNA is mainly single stranded but may include a partial self-complementary structure that can form a double strand.

The miRNA may be isolated or prepared by a standard molecular biological technique, for example, chemical synthesis or recombination, or may be commercially available.

The miRNA molecule may be incorporated into an expression vector. The expression vector encodes the miRNA, preferably in an expressible form. The phrase "in an expressible form" means that the vector expresses the molecule when introduced into host cells. Preferably, the vector may contain a regulatory factor necessary for the expression of the miRNA. The vector may be used for the production of the miRNA or may be directly used as an active ingredient for preventing or treating nicotine addiction or withdrawal symptoms.

The expression vector can be used to stably insert the miRNA into the genome of target cells (see Thomas K R & Capecchi M R, Cell 1987, 51:503-12 for description of homologous recombination cassette vectors). This approach is described, for instance, in Wolff et al., Science 1990, 247:1465-8, U.S. Pat. Nos. 5,580,859, 5,589,466, 5,804,566, 5,739,118, 5,736,524, and 5,679,647, and WO98/04720. Examples of DNA-based delivery technologies include "naked DNA", facilitated (bupivicaine, polymers, peptide-mediated) delivery, cationic lipid complexes, and particle-mediated ("gene gun") or pressure-mediated delivery (see, e.g., U.S. Pat. No. 5,922,687).

The expression vector is preferably a non-viral or viral vector. The non-viral vector is preferably a plasmid DNA. The viral vector is preferably a lentivirus, retrovirus, adenovirus, herpes virus or avipox virus vector but is not limited thereto.

Preferably, the expression vector further includes a selectable marker for easy selection of transformed cells. Examples of such markers include markers that impart selectable phenotypes such as drug resistance, auxotrophy, resistance to cytotoxic agents or the expression of surface proteins, for example, green fluorescent proteins, puromycin, neomycin, hygromycin, histidinol dehydrogenase (hisD), and guanine phosphoribosyltransferase (Gpt).

The expression vector may be introduced into host cells to provide a transformant.

The host cell are preferably somatic cells of mammals, including human beings. The host cells are preferably cells at a human tissue site in need of treatment, for example, human dermal papilla cells, but are not limited thereto.

The expression vector is introduced into host cells by any suitable technique known in the art. For example, the expression vector may be introduced into cells in conjunction with a delivery reagent such as G-fectin, Mirus Transit TKO lipophilic reagent, lipofectin, lipofectamine, cellfectin, cationic phospholipid nanoparticles, cationic polymers, cationic micelles, cationic emulsions or liposomes or may be conjugated with biocompatible polymers such as polyethylene glycol to increase intracellular absorption. However, there is no restriction on the technique for introducing the expression vector into host cells.

The pharmaceutical composition of the present invention may further include or be formulated with at least one pharmaceutically acceptable carrier.

As used herein, the term "pharmaceutically acceptable carrier" refers to an excipient or diluent that does not impair the biological activity and characteristics of an administered compound without irritating an organism. The composition may be formulated with one or more pharmaceutically acceptable carriers to prepare solutions. Suitable pharmaceutically acceptable carriers are sterile biocompatible carriers and examples thereof include saline, sterilized water, Ringer's solution, buffered saline, albumin injectable solution, dextrose solution, maltodextrin solution, glycerol, and ethanol, which may be used alone or as a mixture of two or more thereof. If necessary, the composition may further include other general additives, such as antioxidants, buffers, and bacteriostatic agents. Diluents, dispersants, surfactants, binders, and lubricants may be further added to prepare injectable formulations (such as aqueous solutions, suspensions, and emulsions), pills, capsules, granules, and tablets.

The pharmaceutical composition of the present invention which includes the miRNA as an active ingredient and a pharmaceutically acceptable carrier may be applied to any formulation, for example, a formulation for oral or parenteral administration. Suitable pharmaceutical formulations include those suitable for oral, rectal, nasal, topical (including buccal and sublingual), transdermal, vaginal or parenteral (including intramuscular, subcutaneous, and intravenous) administration, and those suitable for inhalation or insufflation.

Suitable formulations for oral administration including the composition of the present invention as an active ingredient may be, for example, tablets, troches, lozenges, aqueous or oily suspensions, powders or granules, emulsions, hard or soft capsules, syrups, and elixirs.

The composition of the present invention may include a binder such as lactose, saccharose, sorbitol, mannitol, starch, amylopectin, cellulose or gelatin, an excipient such as dicalcium phosphate, a disintegrating agent such as corn starch or sweet potato starch or a lubricant such as magnesium stearate, calcium stearate, sodium stearyl fumarate or polyethylene glycol wax to produce formulations such as tablets and capsules for oral administration. For capsule formulations, the composition of the present invention may further include a liquid carrier such as fatty oil in addition to the above-mentioned material.

Suitable formulations for parenteral administration including the composition of the present invention as an active ingredient may be, for example, injectable formulations such as formulations for subcutaneous, intravenous or intramuscular injection, suppositories, and formulations for spray such as aerosols inhaled through the respiratory tract. The composition of the present invention may be mixed with a stabilizer or buffer in water to prepare a solution or suspension, which may be prepared into unit dosage forms for injection such as ampoules or vials. The composition of the present invention may be prepared into formulations for rectal administration such as suppositories or enemas. In this case, the composition of the present invention may be formulated with a general suppository base such as cocoa butter or another glyceride. The composition of the present invention may be prepared into formulations for spray such as aerosols. In this case, the composition of the present invention may be blended with a suitable additive such as a propellant to disperse a water-dispersed concentrate or wetting powder.

The composition of the present invention may be administered orally or parenterally (e.g., intravenously, intraperitoneally, intramuscularly, intraarterially, intracerebrally, subcutaneously or topically) depending on the intended application. The dose of the composition according to the present invention varies depending on the condition and body weight of patients, the severity of disease, the type of the drug, and the route and time of administration but may be suitably selected by those skilled in the art.

The composition of the present invention is administered in a pharmaceutically effective amount. As used herein, the term "pharmaceutically effective amount" refers to an amount sufficient to treat diseases at a reasonable benefit/risk ratio applicable to any medical treatment. The effective dosage level of the composition may be determined depending on factors, including the type and severity of disease, the activity of the drug, the sensitivity to the drug, the time and route of administration, the rate of excretion, the duration of treatment, and the type of concurrent drugs, and other factors well-known in the medical field. The composition of the present invention may be administered individually or in combination with other therapeutic agents and may be administered sequentially or simultaneously with conventional therapeutic agents. The composition of the present invention may be administered in either single or multiple doses. It is important to administer the composition of the present invention in such a minimum amount that the maximum effect can be achieved without causing side effects in view of all the aforementioned factors. The minimum amount can be easily determined by those skilled in the art.

The concentration of the miRNA is not particularly limited but is from 1 nM to 1 µM, preferably from 1 nM to 100 nM, more preferably from 1 nM to 10 nM.

The content of the miRNA in the expression vector is specifically from 0.01 to 500 mg, more specifically from 0.1 to 300 mg, but is not limited thereto. A recombinant virus containing the miRNA may be used in the present invention. The content of the miRNA molecules in the recombinant virus is specifically from $10^3$ to $10^{12}$ IU (10 to $10^{10}$ PFU), more specifically from $10^5$ to $10^{10}$ IU, but is not limited thereto.

A transformant containing the miRNA may be used in the present invention. The content of the miRNA molecules in the transformant is specifically from $10^3$ to $10^8$, more specifically from $10^4$ to $10^7$, but is not limited thereto.

Another aspect of the present invention is directed to a method for screening a candidate for treating nicotine addiction or withdrawal symptoms including a) treating an animal model having nicotine addiction or withdrawal symptoms with a candidate, b) measuring the expression level of miR-137 in the animal model treated with the candidate, and c) determining whether the candidate increases the expression level of miR-137 compared to an untreated control.

The candidate may be selected from the group consisting of natural compounds, synthetic compounds, RNA, DNA, polypeptides, enzymes, proteins, ligands, antibodies, antigens, bacterial and fungal metabolites, and bioactive molecules.

The animal model having nicotine addiction or withdrawal symptoms includes subjects in which nicotine addiction or withdrawal symptoms have been already observed and subjects in which nicotine addiction or withdrawal symptoms are induced by long-term exposure to nicotine. The animal model may be a mammalian species. Preferred mammalian species include humans, non-human primates, mice, rats, dogs, cats, horses, and cows, but are not limited thereto.

After the animal model having nicotine addiction or withdrawal symptoms is treated with the candidate, the expression level of the miR-137 in a sample from the animal model is measured to investigate the efficacy of the miR-137 in preventing or treating nicotine addiction or withdrawal symptoms. The expression level is measured using biomolecules specifically binding to the miR-137.

The expression level of the miR-137 is measured by any suitable technique known in the art.

The present invention will be explained in more detail with reference to the following examples. However, these examples are not to be construed as limiting or restricting the scope and disclosure of the invention. It is to be understood that based on the teachings of the present invention including the following examples, those skilled in the art can readily practice other embodiments of the present invention whose experimental results are not explicitly presented. Such modifications and variations are intended to come within the scope of the appended claims.

The experimental results of the following examples, including comparative examples, are merely representative and the effects of the exemplary embodiments of the present invention that are not explicitly presented hereinafter can be specifically found in the corresponding sections.

Experimental Example 1: Determination of the Efficacy of miR-137 in Preventing or Treating Nicotine Addiction B6.FVB(Cg)-Tg(Chat-cre)GM60Gsat/Mmucd(ChAT-Cre) male mice, aged ≥7 weeks, were purchased from the Laboratory Animal Resources Center, Korea Institute of Science and Technology (KIST). All animal procedures were performed with the approval of the Animal Care and Use Committee of KIST. The experimental animals were acclimatized to the laboratory environment for at least one week prior to surgery and behavioral abnormalities of the animals were observed. Animals with abnormalities were excluded from this experiment. All experimental animals were housed with a 12-h light/dark cycle and had ad libitum access to water and food in cages under controlled temperature and humidity.

Figure 5:
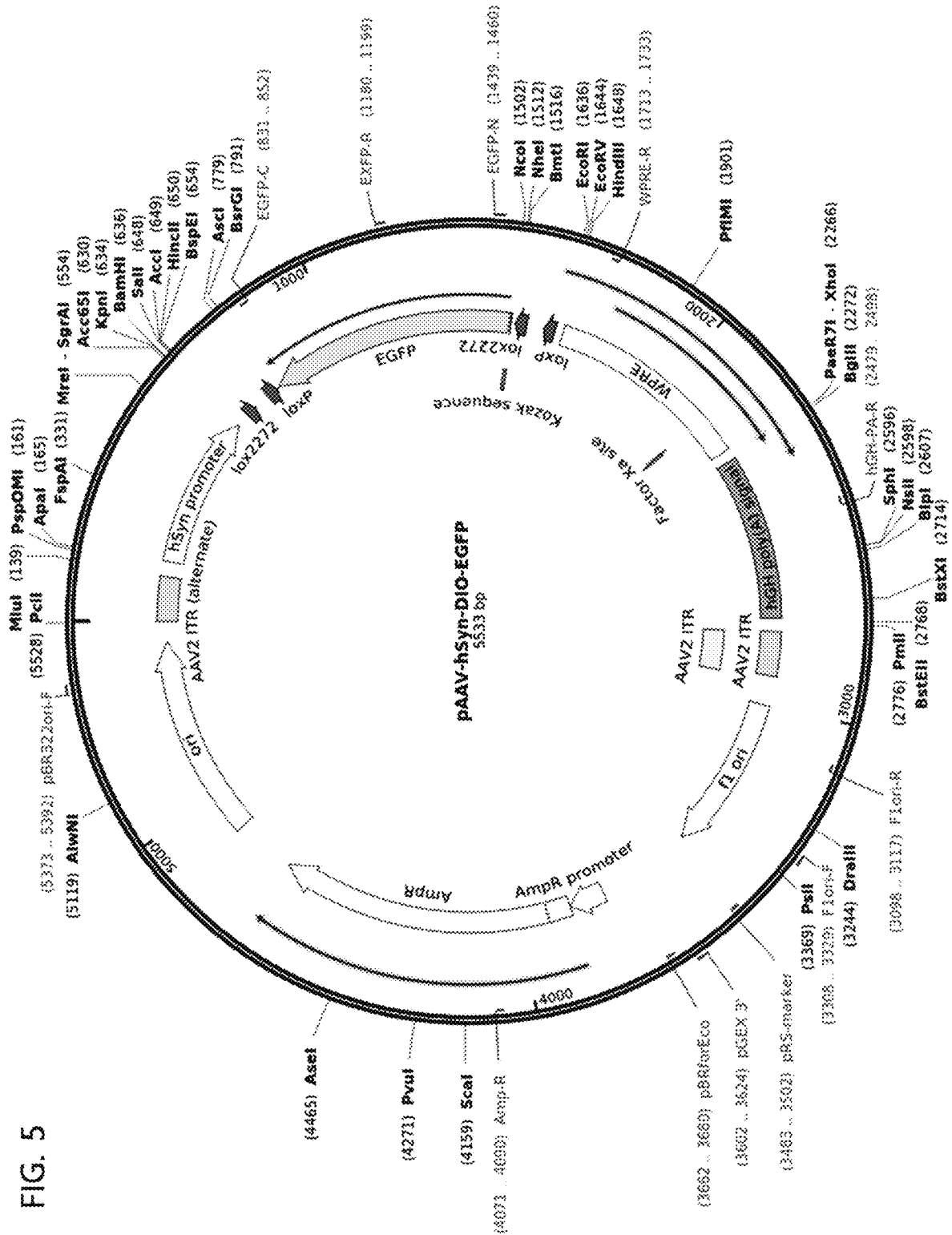
FIG. 5 shows AAV-hSyn-DIO-miR137-eGFP constructed using AAV-hSyn-DIO-eGFP (Addgene).

For an animal experiment, AAV-hSyn-DIO-miR137-eGFP was used for easy synthesis of pre-miR137 transcript. An AAV system was established for long-term expression. Specifically, AAV-hSyn-DIO-miR137-eGFP was constructed using AAV-hSyn-DIO-eGFP (Addgene) (FIG. 5).

The experimental animals were anesthetized with a ketamine-xylazine mixture (ketamine 120 mg/kg, xylazine 8 mg/kg) before opening the scalp and trepanation. Holes were made into the skull using coordinates from bregma: AP +1.1, ML ±1.65 mm. Thereafter, 0.2, 0.7, and 0.7 μl of AAV were injected into coordinates DV −3.0, −2.6, and −2.2 mm, respectively. The injected virus specifically targeted only the cholinergic interneurons of the striatum by Cre-lox recombination. After AAV injection, the holes were closed with silk sutures. The animals were stabilized and infected with the virus for 2 weeks post-surgery. The infected animals were used as an experimental group. The above procedure was repeated except that the same amount of AAV-hSyn-DIO-eGFP where miR-137 was not expressed was injected ("control").

Figure 2:
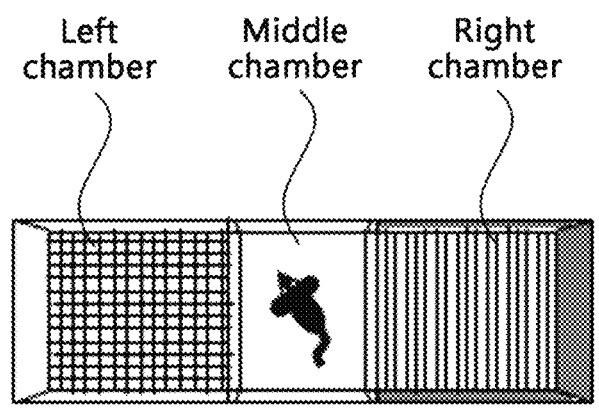
FIG. 2 schematically shows an experimental setup for a conditioned place preference.

In accordance with the design shown in FIG. 1, a conditioned place preference test for nicotine addiction and withdrawal symptoms was conducted on the experimental and control groups. The experimental setup is shown in FIG. 2. The experimental setup consisted of a total of 3 chambers.

On the first day of the test for habituation, each experimental animal was placed in the middle chamber with free access to all three chambers through open doors. The base preference of the experimental animal for each chamber was recorded.

On the second, third, and fourth days of the test, nicotine (0.5 mg/10 ml/kg in saline) and saline were injected twice a day in the morning and afternoon. For higher reliability of the test, the injection order was changed for each experimental animal. Detailed schedules are shown in 1) and 2) of FIG. 1. For example, after the animal injected with nicotine (0.5 mg/10 ml/kg in saline) in the morning was placed in the middle chamber, the door to one of the adjacent chambers was opened (the same door was opened for nicotine injection and the left chamber was used for this test). As soon as the experimental animal entered the left chamber through the open door, the door was closed. The animal was allowed to stay in the left chamber for 20 min. After saline (10 ml/kg) was injected into the mouse in the afternoon, the experimental animal was placed in the middle chamber and the door to the opposite chamber (i.e., the right chamber) was opened. Immediately after the experimental animal entered the right chamber, the door was closed. The animal was allowed to stay for 20 min. This procedure was also repeated on the third and fourth days.

Saline was injected into the control ("Saline-paired") twice a day (each 10 ml/kg).

On the last day, a nicotine addiction preference test was conducted with a video recording. Each of the experimental group ("Nicotine-paired") alternately received nicotine and saline and the control group received saline only was placed in the middle chamber with free access to all three chambers through open doors. The preference (retention time) of the experimental animal for each chamber was recorded. The level of nicotine reward was measured by determining how much the preference of the experimental group for the chamber associated with nicotine increased compared to that of the control.

Figure 3:
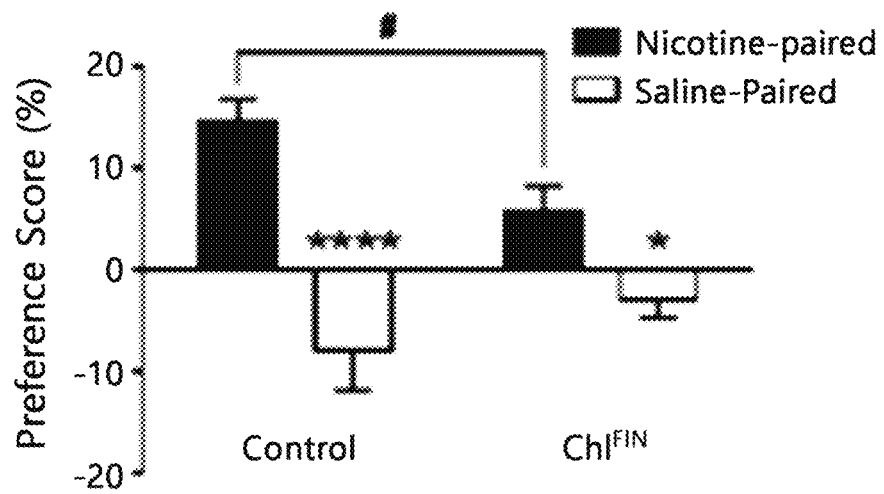
FIG. 3 shows preference scores for nicotine after nicotine injection into an experimental group administered AAV miR-137 and a non-administered control for 3 days to induce nicotine addiction.

FIG. 3 shows preference scores for nicotine after nicotine injection into the experimental group received AAV miR-137 and the non-administered control for 3 days to induce nicotine addiction.

The conditioned place preference score was expressed in percent (%) as the ratio of the preference measured on the last day to that on the first day.

As shown in FIG. 3, the nicotine addiction-induced experimental animal ("Nicotine-paired") received nicotine for 3 days showed high preference for nicotine and the experimental animal received saline only showed no preference for nicotine, indicating that nicotine addiction was sufficiently induced by the experimental procedure employed in the present invention.

In addition, the experimental animal (experimental group) where miR-137 was overexpressed by the injection of AAV-miR-137 into the cholinergic interneurons of the striatum showed at least 2-fold lower conditioned place preference than the control. In conclusion, miR-137 exhibits efficacy in preventing or treating nicotine addiction.

Experimental Example 2: Determination of the Efficacy of miR-137 in Preventing or Treating Withdrawal Symptoms Caused by Nicotine Addiction An experiment for somatic withdrawal signs was conducted as follows.

For an animal experiment, AAV-hSyn-DIO-miR137-eGFP was used for easy synthesis of pre-miR137 transcript. An AAV system was established for long-term expression.

The experimental animals were anesthetized with a ketamine-xylazine mixture (ketamine 120 mg/kg, xylazine 8 mg/kg) before opening the scalp and trepanation. Holes were made into the skull using coordinates from bregma: AP +1.1, ML ±1.65 mm. Thereafter, 0.2, 0.7, and 0.7 µl of AAV were injected into coordinates DV −3.0, −2.6, and −2.2 mm, respectively. The injected virus specifically targeted only the cholinergic interneurons of the striatum by Cre-lox recombination. After AAV injection, the holes were closed with silk sutures. The animals were stabilized and infected with the virus for 2 weeks post-surgery. The infected animals were used as an experimental group ($ChI^{FIN}$). The above procedure was repeated except that the same amount of AAV-hSyn-DIO-eGFP where miR-137 was not expressed was injected ("control").

Nicotine (0.5 mg/10 ml/kg in saline) was injected into the experimental and control groups once a day for 3 days. Mecamylamine (3 mg/10 ml/kg) was administered on the fourth day and indices for mecamylamine-precipitated nicotine withdrawal were checked and recorded. The indices were retropulsion, paw tremor, body shake, and genital licks. The frequencies of the indices for 30 min after the mecamylamine injection were recorded and compared.

Figure 4:
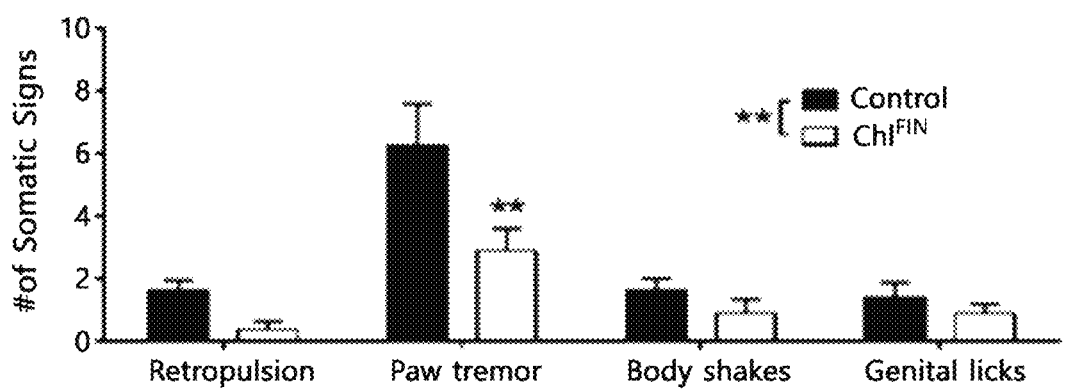
FIG. 4 shows indices for somatic withdrawal signs after nicotine injection into an experimental group administered AAV miR-137 and a non-administered control for 3 days and subsequent mecamylamine injection to induce withdrawal symptoms.

FIG. 4 shows indices for somatic withdrawal signs after injection of nicotine into the experimental group received AAV miR-137 and the non-administered control for 3 days and subsequent mecamylamine injection to induce withdrawal symptoms. The numbers of somatic withdrawal signs in the miR-137-overexpressed experimental group were at least 1.5-2 times smaller than those in the control. In conclusion, miR-137 has efficacy in preventing or treating nicotine addiction and nicotine addiction withdrawal symptoms caused by nicotine addiction.

From these results, it was demonstrated that miR-137 has new prophylactic or therapeutic efficacy for withdrawal behaviors (paw tremor and genital licks), and finally, it significantly reduces the number of paw tremors.

What is claimed is:

1. A method for screening a candidate for treating nicotine addiction or withdrawal symptoms comprising:
   a) treating an animal model having nicotine addiction or withdrawal symptoms with a candidate;
   b) measuring the expression level of miR-137 in the animal model treated with the candidate;
   c) determining whether the candidate increases the expression level of miR-137 compared to an untreated control; and
   d) administering the candidate containing miR-137 to a patient for treating the nicotine addition or the withdrawal symptoms if the candidate increases the expression level of miR-137 compared to the untreated control.

2. The method according to claim 1, wherein the miR-137 has the sequence set forth in SEQ ID NO: 1.

* * * * *

SEQUENCE LISTING

```
<160> NUMBER OF SEQ ID NOS: 1

<210> SEQ ID NO 1
<211> LENGTH: 102
<212> TYPE: DNA
<213> ORGANISM: Artificial Sequence
<220> FEATURE:
<223> OTHER INFORMATION: Homo sapiens microRNA 137 (MIR137), microRNA

<400> SEQUENCE: 1
ggtcctctga ctctcttcgg tgacgggtat tcttgggtgg ataatacgga ttacgttgtt      60
attgcttaag aatacgcgta gtcgaggaga gtaccagcgg ca                        102
```